United States Patent [19]

Baresel et al.

[11] 4,194,994

[45] Mar. 25, 1980

[54] SINTERED METAL OXIDE SEMICONDUCTOR HAVING ELECTRICAL CONDUCTIVITY HIGHLY SENSITIVE TO OXYGEN PARTIAL PRESSURE

[75] Inventors: Detlef Baresel, Stuttgart; Peter Scharner, Leonberg; Gerhard Huth, Stuttgart; Winfried Gillert, Ludwigsburg, all of Fed. Rep. of Germany

[73] Assignee: Robert Bosch GmbH, Stuttgart, Fed. Rep. of Germany

[21] Appl. No.: 845,796

[22] Filed: Oct. 26, 1977

[30] Foreign Application Priority Data

Oct. 26, 1976 [DE] Fed. Rep. of Germany ....... 2648373

[51] Int. Cl.$^2$ ............................................. H01B 1/08
[52] U.S. Cl. ..................................... 252/518; 252/521; 23/232 E
[58] Field of Search ....................... 252/521, 518, 408; 23/232 E, 254 E; 338/34; 422/94–98, 119

[56] References Cited

U.S. PATENT DOCUMENTS

| 3,611,243 | 10/1971 | Hardtl | 338/34 |
|---|---|---|---|
| 3,732,519 | 5/1973 | Taguchi | 338/34 |
| 3,932,246 | 1/1976 | Stadler et al. | 23/254 E X |

Primary Examiner—E. Suzanne Parr
Attorney, Agent, or Firm—Frishauf, Holtz, Goodman & Woodward

[57] ABSTRACT

Tin oxide doped with magnesium oxide or niobium pentoxide and prepared as a sintered material is found to be highly sensitive to oxygen partial pressure both in the presence of free oxygen and in the presence of oxidizable gases, such as carbon monoxide or the lower oxides of nitrogen, and even in the presence of mixtures of both, such as in the exhaust gas of an internal combustion engine. The electrical conductivity varies by substantially more than an order of magnitude in response to a change in the oxygen partial pressure of about one-half an order of magnitude. The doped oxides operate as poor catalysts for the oxidation of oxidizable components of the exhaust gases. Chromium oxide doped with tin oxide shows the effect of an excessively good catalysis from the point of view of range of measurement, but is usable to give a sharp indication of the appearance or disappearance of free oxygen in a gas mixture. Zinc oxide doped with aluminum oxide has a conductivity that is good for measuring the content of free oxygen, but is of questionable value in the presence of a substantial concentration of carbon monoxide.

1 Claim, 7 Drawing Figures

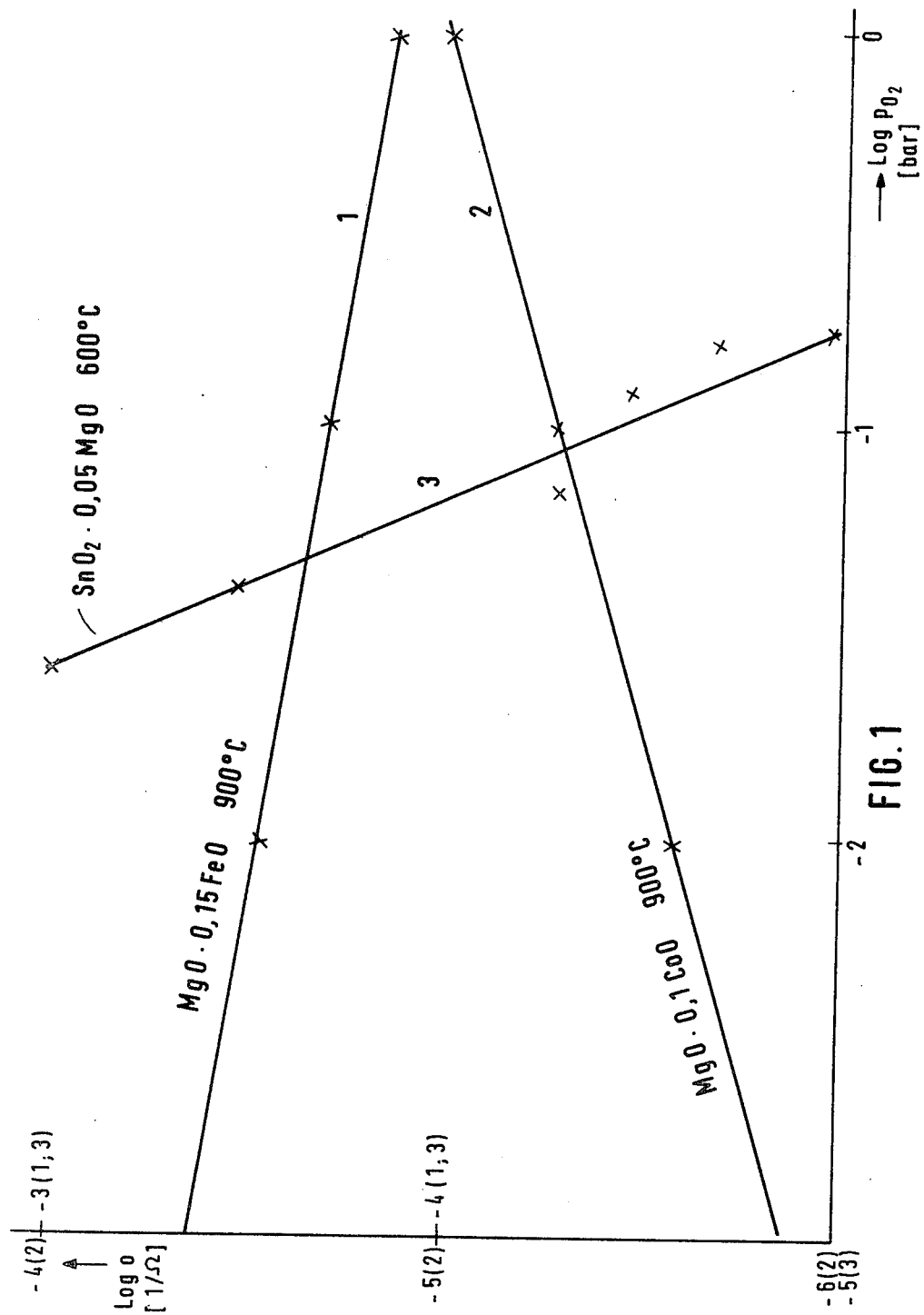

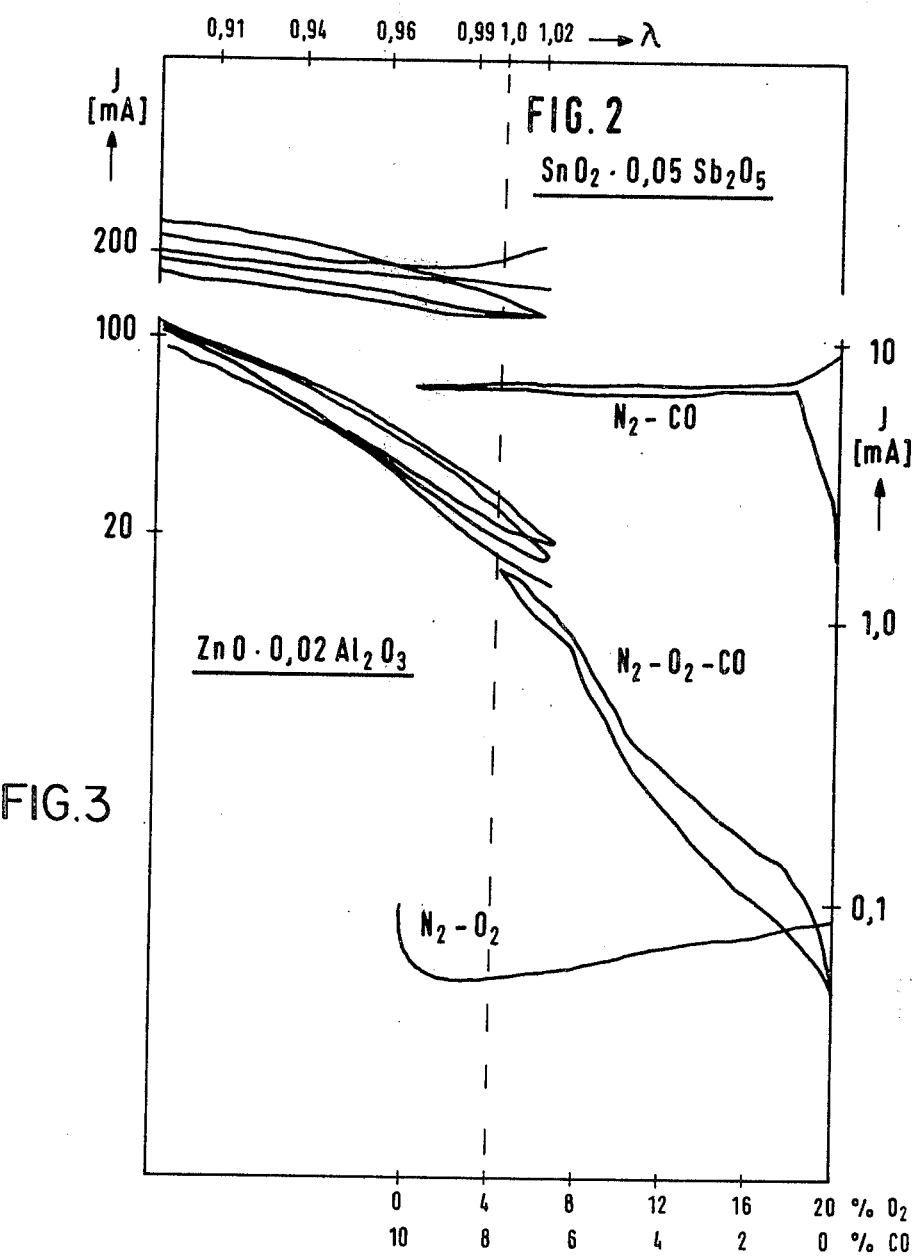

SINTERED METAL OXIDE SEMICONDUCTOR HAVING ELECTRICAL CONDUCTIVITY HIGHLY SENSITIVE TO OXYGEN PARTIAL PRESSURE

This invention relates to semiconductor sensors for the determination of the oxygen and/or oxidizable components (such as carbon monoxide and the lower oxides of nitrogen) in exhaust gases by means of the change of the electrical conductivity of the semiconductor.

BACKGROUND AND PRIOR ART

It is a requirement for the use of semiconductors in such sensors that the conductivity should have a relatively low temperature dependence as well as a very strong change of conductivity ($\Delta\delta$) in response to the concentration of the gases just mentioned in exhaust gas. Engine exhaust gas contains as noxious components in the case of rich mixture mainly carbon monoxide (0.2 to 8% CO), whereas oxygen predominates in the case of lean mixtures (0.5 to 3% $O_2$), while the $NO_x$ content for fuel-air ratios $1.01 < \lambda < 1.2$ can at most reach 0.4%.

Since in the case of rich mixtures the detection of CO is of first importance among the requirements for producing a warning signal, in the case of lean mixtures the determination of the $O_2$ concentration, for example for the control of a backfire trap or for operating an internal combustion motor on a mixture that is an lean as possible, requires responsiveness to free $O_2$ as well as to CO, so that both these responses are of primary importance.

The conductivity change $\Delta\sigma$ resulting from the equilibrium between gaseous oxygen and oxygen bound in the semiconducting oxide lattice is given according to semiconductor theory by the equation $$\Delta\sigma \sim p_{O_2} \pm 1/n \tag{1}$$

for the values $n \geq 4$. For the case of conductivity change resulting from adsorption, for $O_2$ the value of n can also be 2 (oxygen ions with a single negative charge), and/- for CO the equation holds with $n \geq 2$. This appears in curves 1 and 2 of FIG. 1, in which the measured conductivity ($\sigma$) is plotted against the oxygen partial pressure ($p_{O_2}$) on a log-log graph (both scales logarithmic). Curve 1 shows the relationships in the case of a semiconductor of MgO with 15 mol % FeO at 900° C. Curve 2, on the other hand, shows the corresponding relations for a semiconductor of MgO with 10 mol % CoO, likewise at 900° C. In the case of curve 1, the relation found is:

$$d \log \sigma / d \log p_{O_2} = -1/5.75 = -0.17$$

whereas this relation in the case of curve 2 is evaluated at $+1/3.5 = 0.29$. In the case of these pure semiconductor oxides there is accordingly found, for a change of the oxygen partial pressure of about $\frac{1}{2}$ order of magnitude, a change of conductivity of only $\frac{1}{3}$ order of magnitude. This relatively low change of the electrical conductivity is in general too small for warning signals within the range of concentration variations that occur in practice in exhaust gases and they can be utilized only with great electrical measurement expense and complication, provided that there is small temperature dependence of the electrical conductivity or provided that this temperature dependence is compensated by a second sensor that is electrically identical with the first. For a regulating or control operation, therefore, these cnductivity differences are insufficient.

THE PRESENT INVENTION

It is an object of the present invention to find a semiconductor type of sensor for the oxygen or oxidizable content of engine exhaust gases that will provide a greater change in the conductivity of the semiconductor with a change of oxygen partial pressure than has been available heretofore.

Briefly, a tin oxide matrix is doped with magnesium oxide or niobium pentoxide, the doping being preferably from 0.1 to 20 mol % MgO or $Nb_2O_5$. With such materials, if the oxygen partial pressure in the aggregate exhaust gas volume changes by about $\frac{1}{2}$ order of magnitude, the change in electrical conductivity of the semiconductor amounts to at least one full order of magnitude. More generally, the invention depends upon the utilization of a tin oxide semiconductor matrix doped with another metal oxide so that the electrical conductivity in the presence of oxygen and the oxidizable components of a gas in contact with the semiconductor, the conductivity changes approximately linearly with the gas composition, with a sensitivity such that the electrical conductivity change is at least one full order of magnitude when the oxygen partial pressure in the aggregate exhaust gas volume changes by about $\frac{1}{2}$ order of magnitude.

BRIEF DESCRIPTION OF THE DRAWINGS

FIG. 1 shows the sensitivity of an illustrative example of a semiconductor composition according to the invention, compared to previously known materials;

FIG. 2 shows the dependence of conductivity upon carbon monoxide gas content, of tin oxide doped with a dopant outside the invention; and FIGS. 3–7 are graphs showing the sensitivity of various compositions according to the invention, plotting conductivity against oxygen or carbon monoxide content, the graph of FIG. 6 covering a more lmited range of oxygen and carbon monoxide content.

Figure 4:
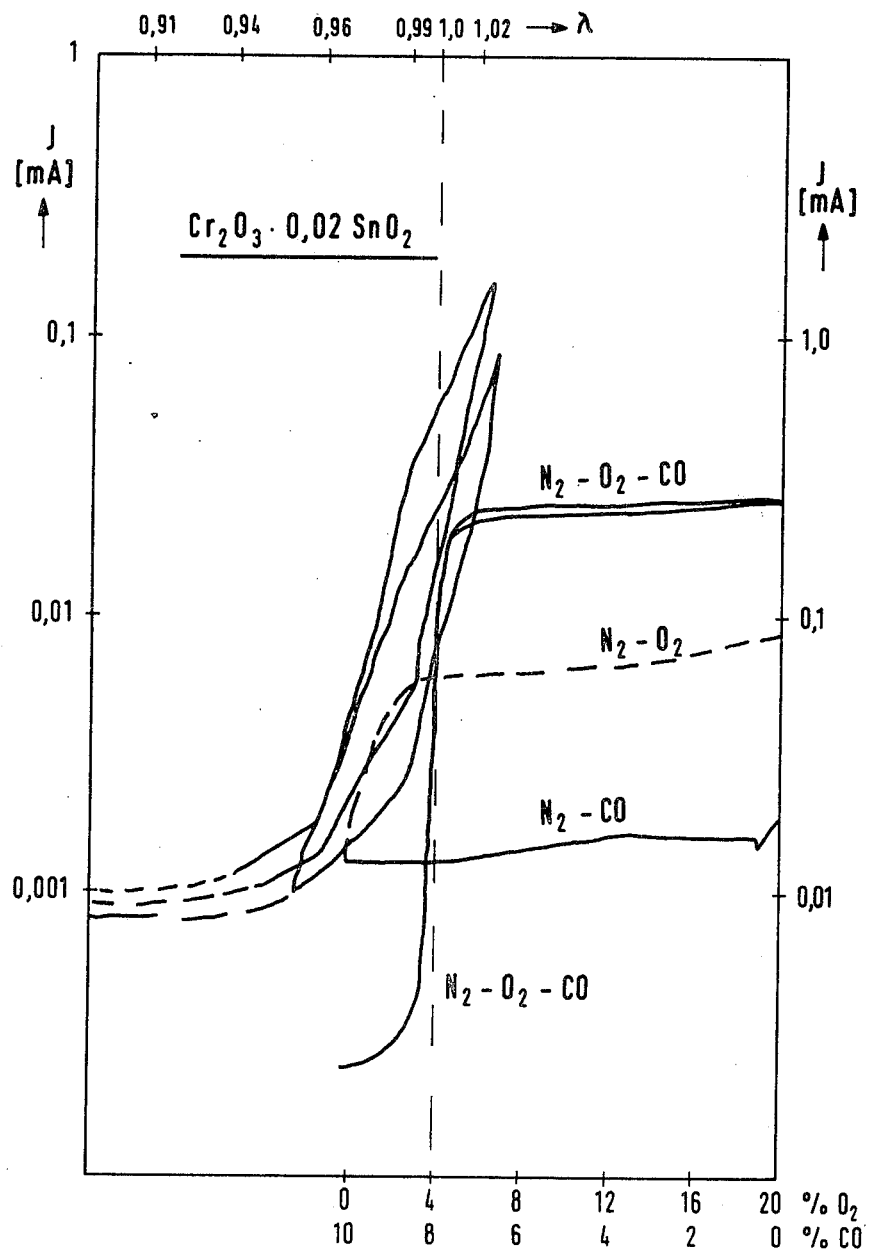

The semiconductor sensors of the present invention have sufficient sensitivity to make them usable for warning devices or regulating and control devices. Their outstanding sensitivity is shown, for instance, in curve 3 of FIG. 1 which illustrates the example of a semiconductor according to the invention consisting of tin oxide with 5 mol % MgO. In the case of a change of oxygen partial pressure of approximately $\frac{1}{2}$ an order of magnitude, the conductivity changes by 2 orders of magnitude. This can be expressed in the relation $$d \log \sigma / d \log p_{O_2} = -3.5.$$

This dependence of the electrical conductivity on the oxygen partial pressure is not to be explained merely by the semiconductor theory from which equation (1) came. In this case, there appears rather an analogous amplification of the concentration change of the gases to be measured, oxygen and an oxidizable gas, for example carbon monoxide. This amplification is obtained by means of a weak catalysis on the surface of the semiconductor which nevertheless must not be so effective as to reach suddenly the equilibrium of the corresponding reaction for example according to the equation

That is possible forexample in the case of strongly different adsorption or chemisorption of the different gases or by dissociation steps of differing speed of the mechanisms of adsorption on the solid surface or by differential reaction mechanisms (Langmuir-Hinshelwood, Eley-Rideal). The above mentioned analog amplification of the measuring signal accordingly depends therefore upon the chemical preparation of the semiconductor utilized for sensors in such a manner as to provide a weak catalytic effect. The combination of semiconduction and rather poor catalyzation effect which lies at the base of the present invention must be obtained by a certain chemical composition of the semiconductor, so that the semiconduction can be influenced both by chemisorption and by removal or incorporation of oxygen in the lattice of the semiconductor.

As a byproduct of the invention, other doped metal oxides have been found with remarkable and reliable sensivity to oxygen content over a narrower range of gas composition, namely ZnO doped with $Al_2O_3$ and $Cr_2O_3$ doped with $SnO_2$ as further described below.

FIGS. 2 to 7 show how the combination of these two properties works out in the case of oxide semiconductors. The axis of ordinates of these figures is in each case the measured sensor current in milliamperes in the case of an applies dc voltage of 12 volts, which is plotted as a measure of conductivity, whereas the axis of abscissae provides a scale of exhaust gas composition. The data provided at the right hand and lower axes relate to laboratory measurements with synthetic "exhaust gas" (mixtures of $N_2$—$O_2$ or $N_2$—CO or $N_2$—$O_2$—CO) and relate to the curves that are tangent to these axes. The left hand and upper axes and the curves touching them reproduce the results of experiments with actual exhaust gas of an internal combustion engine operating with lead-free high-test fuel with both rich and lean mixtures (engine speed 3060 r.p.m., torque 8 to 11 kp, electronic injection $\lambda$ sonde for mixture measurement). The stoichiometric points of both classes of experiments ($\lambda = 1$ or $2 \times$vol. % $O_2$ = vol. % CO) lie on the abscissae at the same position, whereas the units of the two scales of abscissae are of different magnitudes. The change from rich to lean mixtures during the motor test was carried out three times within six hours. The curves of the laboratory tests in each case contain 12 to 15 measuring points per curve sequence, with each measuring point taken 5 minutes after adjustment of the gas mixture.

FIG. 2 shows the results of the motor experiment with a semiconductor ($SnO_2$ doped with 5 mol % $Sb_2O_5$), the conductivity of which only weakly reacts to CO excess ($\lambda < 1$) and to $O_2$ excess ($\lambda > 1$), more or less as in the case of an oxide semiconductor would react to oxygen partial pressure in accordance with curves 1 and 2 of FIG. 1, i.e. in accordance with equation (1). Laboratory tests were superfluous in this case.

FIG. 3, relating to a semiconductor of ZnO doped with 2 mol % $Al_2O_3$, shows a somewhat linear dependence that is repeated in the laboratory test for the $N_2$—$O_2$—CO mixture, while for $O_2$ or CO alone, no conductivity changes of that kind are obtained. In this case evidently on account of the very poorly catalyzed reaction (2) there was a tendency to produce a constant percentage reduction of adsorbed CO in the rich mixture region and of adsorbed $O_2$ in the lean mixture region, so that a linear rise of the conductivity with the CO concentration resulted and the surface was not, as in the case of pure $N_2$—CO, already fully coated with a layer of CO at low CO concentration, so that with further increasing CO concentration the CO molecules impinging on the surface of the semiconductor could no longer influence the conductivity. This system shows, over the entire region from rich to lean, a practically linear dependence of the electrical conductivity of the gas composition. It could thus represent both a good CO sensor and also a good $O_2$ sensor, yet in the rich mixture region there is the danger that zinc oxide will gradually be reduced by CO, so that utilization as a CO sensor is not to be recommended. In the lean mixture region, where only subsidiary amounts of carbon monoxide are present, this system is nevertheless very well usable as a sensor.

FIG. 4 shows the characteristic curve of a catalytically too active semiconductor ($Cr_2O_3$ doped with 2 mol % $SnO_2$) which indeed shows a large conductivity jump at $\lambda = 1$, and therefore is unsuitable for the purpose of this invention.

The examples given up to now do not yet show or show only partly the behavior of semiconductors according to the invention, but they nevertheless serve to explain the principle according to which the semiconductors of the present invention operate. The following examples now show the manner of operation of the semiconductors of the present invention.

DESCRIPTION OF THE INVENTION

Figure 5:
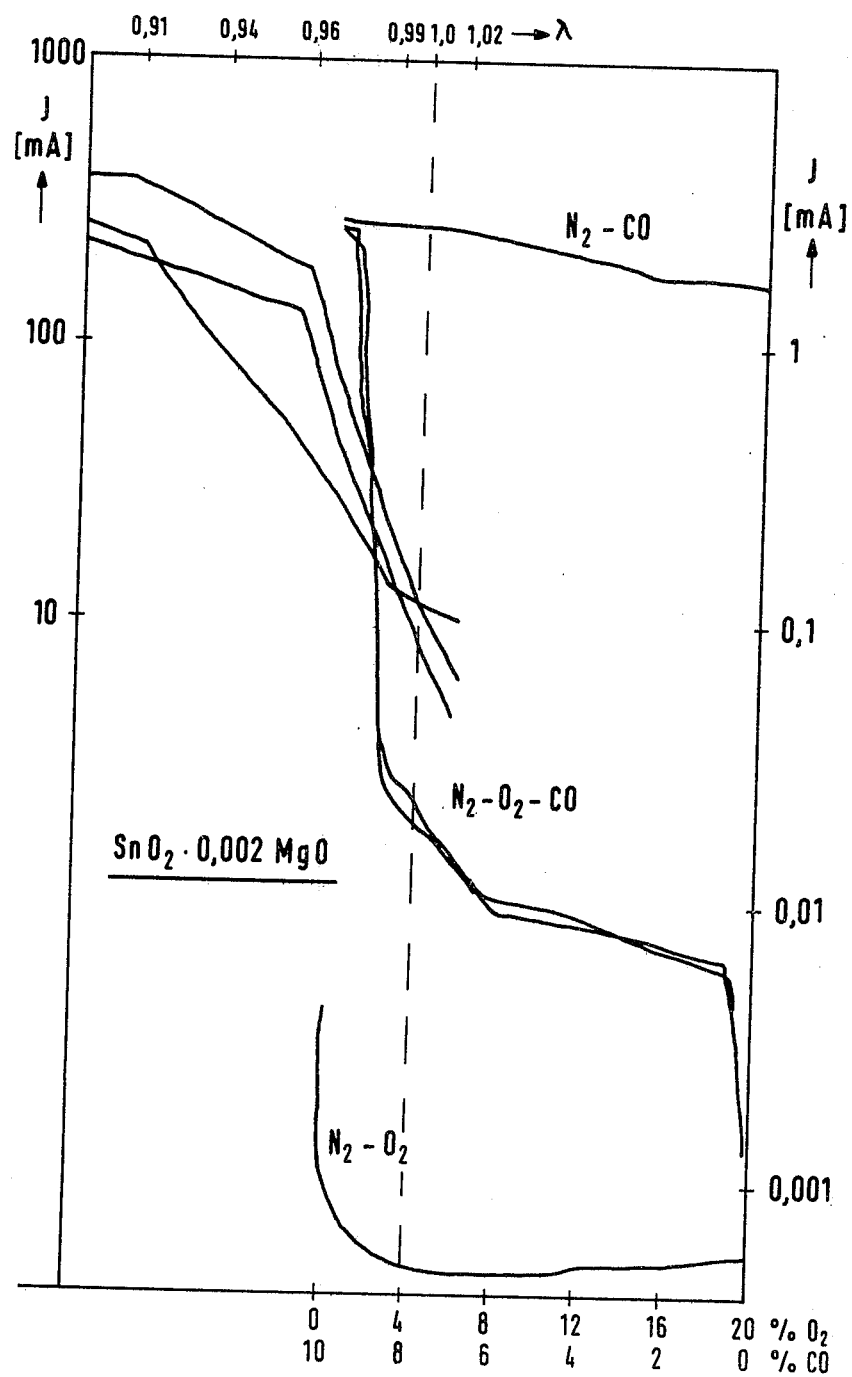

FIG. 5, relating to $SnO_2$ doped with 0.2 mol % MgO shows the results of a semiconductor responding weakly in its conductivity behavior to CO and responding strongly to small contents of $O_2$. Here also the catalytic oxidation of CO is weak up to about 9 mol % CO and delivers relatively large signals by the conductivity change. Since the conductivity is influenced strongly by $O_2$ only between 0 and 3 mol %, and otherwise depends only little on $O_2$ and CO, this system can be put into service both as a sensor for small oxygen contents, which is to say for the lean mixture range, and also as a CO sensor in the presence of oxygen.

Figure 6:
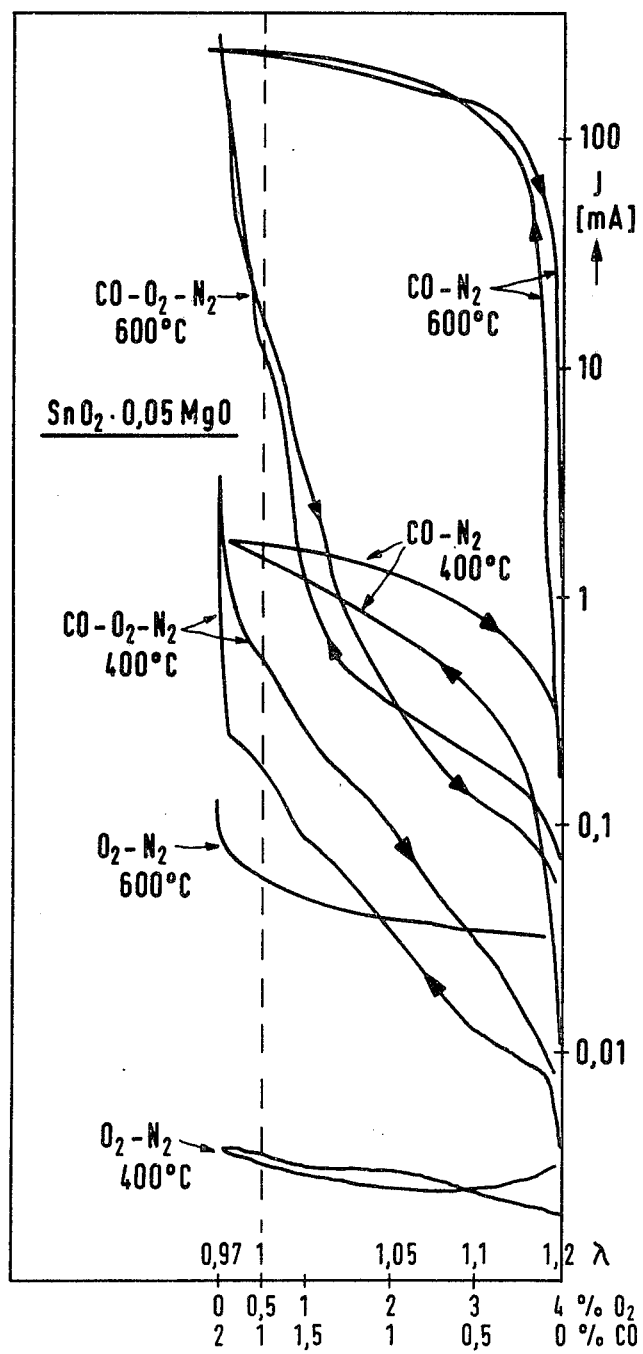
Figure 7:
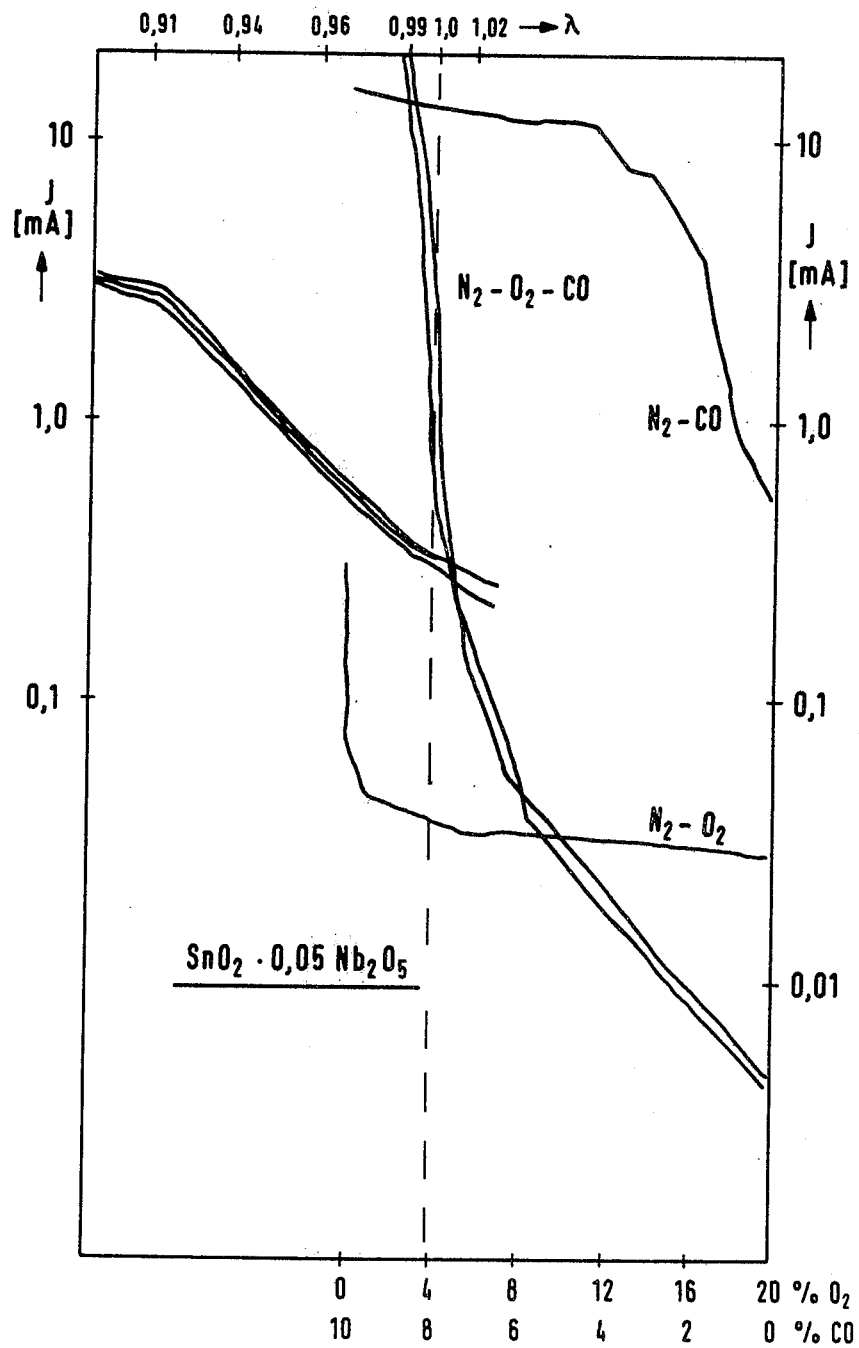

FIG. 6 shows a further impairment of the catalysis of reaction (2) with increased doping with MgO (in this case $SnO_2 + 5$ mol % MgO) and therefore a very favorably usable characteristic; here the desired sensitivity is obtained in the very concentration range of oxygen and carbon monoxide that corresponds to operation of an internal combustion engine in the lean mixture range ($1.0 < \lambda < 1.2$). This favorable relation for CO or $O_2$ indication is even more remarkable in the case of the sensor of $SnO_2$ doped with 5 mol % $Nb_2O_5$, the results of which are shown in FIG. 7. Here, there is the possibility to determine the oxygen content in the lean range of the exhaust gas and CO in rich mixtures both individually, in inert atmospheres, and also in mixtures with each other. The resulting values of the conductivity changes are large enough for further processing of the electric response to produce warning or measurement signals. The behavior of this material in actual exhaust gas of a gasoline engine showed in the first experiment a good to very good duration of serviceability over 6 hours between 400° and 600° C. The semiconductors, with which the results shown in FIGS. 4, 5 and 7 were obtained, were produced as follows:

EXAMPLE 1. $Cr_2O_3.0.02\ SnO_2$ 157 g of chromium nitrate $Cr(NO_3)_3.9\ H_2O$ were dissolved with 0.892 g of tin chloride $SnCl_2.2\ H_2O$ in 2500 ml $H_2O$ and precipitated within one hour with stirring at 80° C. with about 90 ml of 25% $NH_4OH$. The material was stirred for an additional hour at the same temperature. The pH value was about 8. The precipitate was then centrifuged out, three times washed with distilled ammoniated water, dried at 300° C. for two hours and sintered for 17 hours at 850° C. Tablets were pressed from the powder under a pressure of $3.10^3$ bar (diameter 6 mm, 1 mm), and the tablets were once again sintered for two hours at 850° C.

EXAMPLE 2. $SnO_2.0.002$ MgO 23.7 g of granulated tin was dissolved with 0.1 g of magnesium nitrate $Mg(NO_3)_2.6$ $H_2O$ in 100 ml of concentrated $HNO_3$ and evaporated with warming and stirring until dry. The residue was then tempered for 20 hours at 500° C. Tablets were made of the powder of the same size and with the same pressure as in Example 1 and sintered at 650° C. for two hours.

EXAMPLE 3. $SnO_2.0.05$ $Nb_2O_5$

In a 1 liter three-necked flask with stirrer, drop-dispensing funnel and reflux condenser, 45 g of oxalic acid was dissolved in about 400 ml of 5% hydrochloric acid. While stirring the solution, 24.7 g of $SnCl_4$ were added drop by drop. To this solution, a solution of 2.7 g of $NbCl_5$ in 5 g of oxalic acid solution in hydrochloric acid were added. The mixture was evaporated on a sand bath in a porcelain dish until dry, dried at 150° C. and then tempered for 8 hours at 500° C. and for 72 hours at 850° C. Tablets were passed from the powder in the manner described in Example 1, which were then sintered for two hours at 850° C.

For the provision of contacts, the tablets were pressed between two gold contacts, with the entire assembly located in a holder capable of being screwed into the exhaust pipe of an internal combustion engine or into an experimental apparatus providing a flow of synthetic $\mp$exhaust gas" in the manner similar to that used for the known measuring sensors provided on the principle of bionically conducting solid electrolytes such as stabilized zirconium dioxide. A dc voltage of 12 volts was applied between the contacts and the electrical resistance of the assembly was measured as a measure of the electrical conductivity of the semiconductor.

We claim:

1. A semiconductor composition for sensors responsive to oxygen partial pressure in automotive exhaust gas with which the composition is in contact by a change in electrical conductivity, said composition consisting essentially of tin oxide doped with 0.2 to 20 mol% of an oxide selected from the group consisting of magnesium oxide and niobium pentoxide and having a conductivity characteristic which is approximately linear with respect to the oxygen content of said gas and substantially less catalytic effect on the oxidation of carbon monoxide than undoped tin oxide and which provides a change of electrical conductivity of at least one order of magnitude when the oxygen partial pressure in said gas changes by approximately one-half an order of magnitude.

* * * * *